United States Patent [19]

Pickens

[11] Patent Number: 5,507,185
[45] Date of Patent: Apr. 16, 1996

[54] ADAPTIVE SCANNING TECHNIQUE FOR ULTRASONIC TESTING UTILIZING REALTIME LIFT-OFF DETECTION

[75] Inventor: Keith S. Pickens, San Antonio, Tex.

[73] Assignee: Southwest Research Institute, San Antonio, Tex.

[21] Appl. No.: 32,337

[22] Filed: Mar. 16, 1993

[51] Int. Cl.$^6$ ................................................. G01N 29/26
[52] U.S. Cl. .................... 73/620; 73/627; 73/634
[58] Field of Search ........................... 73/620, 618, 619, 73/634, 635, 633, 622, 636, 586, 638, 639, 629

[56] References Cited

U.S. PATENT DOCUMENTS

| | | | |
|---|---|---|---|
| 3,086,390 | 4/1963 | Brown | 73/67.8 |
| 4,041,379 | 8/1977 | Karlsson | 324/37 |
| 4,043,185 | 8/1977 | Siebert | 73/67.7 |
| 4,044,594 | 8/1977 | Owens et al. | 73/636 |
| 4,237,901 | 12/1980 | Taenzer | 128/660 |
| 4,470,307 | 9/1984 | Genter | 73/634 |
| 4,689,995 | 9/1987 | Turbe | 73/636 |
| 5,031,458 | 7/1991 | Young et al. | 73/636 |

FOREIGN PATENT DOCUMENTS

| | | | |
|---|---|---|---|
| 523348 | 7/1976 | U.S.S.R. | 73/634 |
| 1221594 | 3/1986 | U.S.S.R. | 73/620 |

*Primary Examiner*—Hezron E. Williams
*Assistant Examiner*—Nashmiya Ashraf
*Attorney, Agent, or Firm*—Gunn, Lee & Miller

[57] ABSTRACT

An adaptive scanning technique for ultrasonic testing of materials utilizing a realtime lift off detection system. The technique recognizes characteristic reflected/generated signals of partial and total lift off occurrences, wherein the ultrasonic transducer is separated from the surface of the test material. Once recognized and analyzed, these characteristic reflected signals are correlated with parameter changes preselected to compensate for such partial or total lift off occurrences. These parameter changes are communicated to a mechanical positioning system that alters the position, scanning speed, and vertical force with which mechanical compliance of the transducer is maintained with the test material.

5 Claims, 3 Drawing Sheets

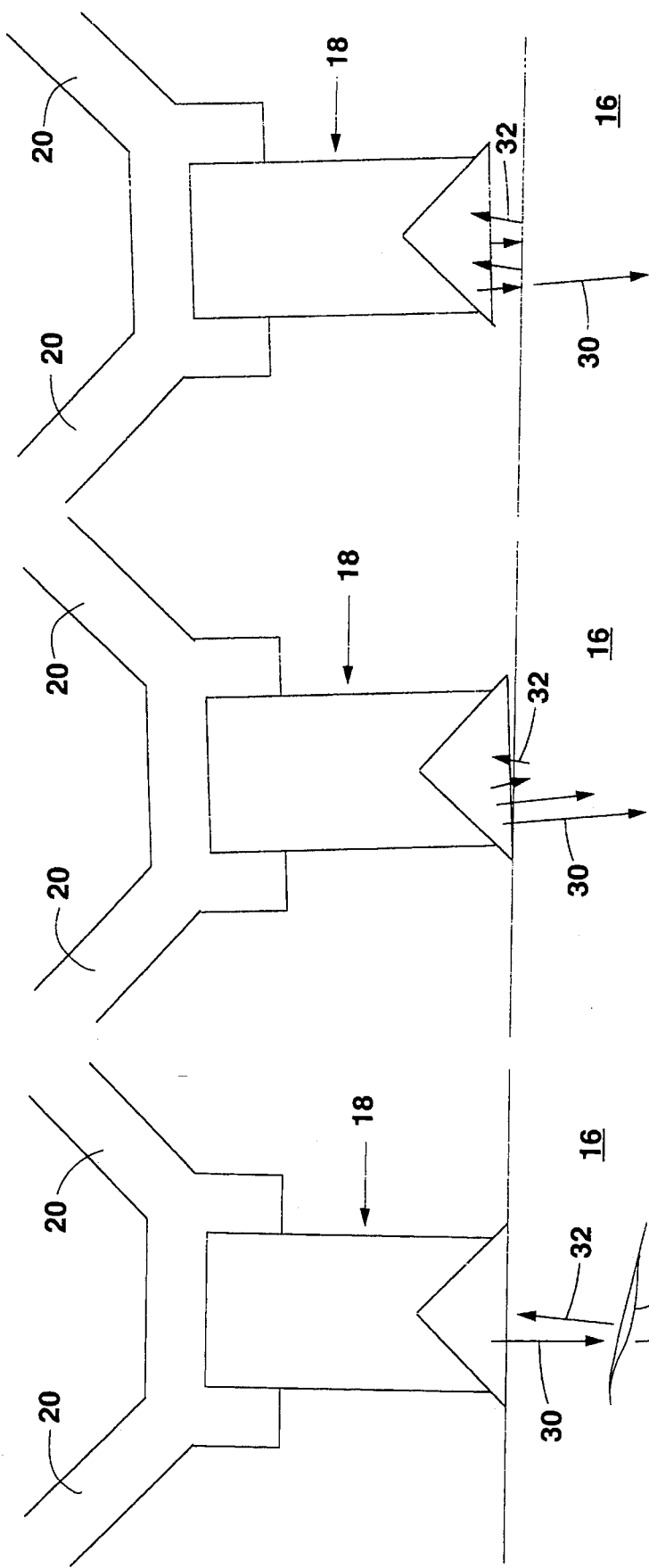

ADAPTIVE SCANNING TECHNIQUE FOR ULTRASONIC TESTING UTILIZING REALTIME LIFT-OFF DETECTION

BACKGROUND OF THE INVENTION

1. Field of the Invention

The present invention relates generally to non-destructive evaluation (NDE) of materials. The present invention relates more specifically to a scanning technique for ultrasonic testing of materials that utilizes a realtime means for addressing loss of transducer contact with the material being evaluated.

2. Description of the Prior Art

One of the most frequently utilized techniques for the non-destructive evaluation of materials is the analysis and testing of the material through a systematic scan across the surface of the material with an ultrasonic transducer. Typically, this involves the use of a transducer that both transmits a generated ultrasonic signal and receives reflected and generated signals back from irregularities or anomalies hidden within the subject material. Appropriate interpretation of the received signals can aid in a description of the size, structure, distance, shape, and location of faults, cracks, or other anomalies.

The ability to accurately interpret information contained within the reflected and generated signals by the use of ultrasonic analyzing equipment requires that some baseline background signal, to some degree consistent over time, be established. If outside factors enter into the characteristics of the reflected and generated signals, then the interpretation and isolation of relevant data within the signals becomes quite difficult.

One such outside factor that can complicate the return signal is the occurrence of what is referred to as a "lift off" of the ultrasonic transducer from the surface of the material being tested. This lift off is simply the partial or complete loss of direct contact between the ultrasonic transducer and the material during scanning. Loss of transducer contact may be due to imperfections in the method of placing the transducer against the material, or may simply be the result of irregularities in the surface of the material. Lift off may, therefore, be caused by the mechanical positioning system that moves the transducer about the material, as well as by the properties of the material itself. Both of these factors which effect lift off will, of course, be position dependent. The mechanical loading will vary with the orientation of the positioning system and the structure of the specific positioning mechanism. The surface of the material will vary from point to point as a function of its manufacture and/or its wear over time.

Ultrasonic waves travel as longitudinal or shear waves in elastic materials. The speed of the ultrasonic wave depends upon the elasticity and density of the transmitting medium. Therefore, different mediums will transmit ultrasonic waves at rates that are characteristic of the substance.

Ultrasonic testing is possible because ultrasonic waves travel at different speeds through different mediums. By transmitting and receiving ultrasonic waves and tracking the time period over which these transmissions and receptions are made, a great deal can be understood about the medium through which the ultrasonic wave is traveling. Where the medium changes, such as where an anomaly or inclusion exists within a substance, the direction and speed of the ultrasonic wave is altered in a way that is indicative of some characteristic of the anomaly or inclusion. An ultrasonic transducer may be used to transmit ultrasonic waves into the material to be tested, and the reflected signal may be analyzed so as to detect and identify an irregularity within the material.

If the transducer is not in direct contact with the material to be tested, the first change in medium that the transmitted signal encounters is the interface between the transducer and the air space above the specimen. This interface will, therefore, create the first reflected and/or generated signal that is received back by the transducer. It is possible to misinterpret this received signal as indicative of some property of the specimen, rather than merely the occurrence of a lift off event. Since ultrasonic waves do not enter the specimen during the lift off event, irregularities in the specimen cannot be detected.

The loss of contact between the material and an ultrasonic transducer can result in a large localized change in the acoustic impedance seen by the analysis instrumentation. This change provides a significant detectable signal that must be distinguished from other anomaly sourced signals in order to be properly identified as resulting from a lift off event.

Previous attempts to address the problem of transducer lift off have been concerned primarily with minimizing its occurrence. Efforts to prevent lift off from the test material's surface, have attempted to maintain transducer contact by way of devices that adjust the transducer for irregularities in the surface, or by utilizing transducers whose transmitting and receiving face is flexible and/or configurable to the surface of the material. Unfortunately, these methods assume that certain expected irregularities will be encountered in the material's surface or that some normal inaccuracies in the mechanical positioning system used to scan the transducer across the surface will occur. None of the attempts thus far to consider the effect of lift off provide any realtime sensing or analysis of the phenomena, and are therefore subject to sometimes gross inaccuracies in handling signals that result from such lift off.

There have been some attempts, as mentioned above, to provide mechanisms whereby ultrasonic transducers may be accurately positioned and monitored with respect to the surface of the test material. U.S. Pat. No. 4,041,379, issued to Karlsson, discloses such an apparatus, wherein the inspecting ultrasonic transducers are held by means of pressure and tension members which are carried by a common support arm. The position, pressure, and tension of the transducer are independently controllable, and allow each transducer to be established with a predetermined force against the material surface.

U.S. Pat. No. 3,086,390, issued to Brown, describes an ultrasonic system intended for use in the medical field that utilizes an assembly of springs and weights to control the position of ultrasonic transducers on the non-planar surface of the human body. This system is designed to maintain a consistent contact with the skin of the patient undergoing analysis, despite the normal irregularities in the skin surface.

U.S. Pat. No. 4,043,185, issued to Siebert, discloses an ultrasonic transmitter and receiver that is supported by a device adapted to direct the transducer towards the surface of the material with a specific force, or to elevate the transducer in a manner that reduces the force against the material being tested.

Some designs such as that disclosed in Soviet Union Patent No. 1221594A control a nominal gap between the ultrasonic transducer and the test material so that the effect of surface irregularities is reduced to some extent.

Attempting to address the same problem but compensating for surface irregularities in a different way is U.S. Pat. No. 4,237,901, issued to Taenzer. The Taenzer patent describes an ultrasonic scanning system whose probe is a fluid filled transducer with a flexible surface that imparts a passive pressure against the material being tested. Irregularities in the surface of the material do not normally induce lift off, but only deform the face of the transducer. Unfortunately, this design is limited to certain specific applications, and is not appropriate for any broad range of materials testing concerns.

In general, the previous attempts to address the lift off problem in ultrasonic NDE testing have focussed on eliminating or at least reducing the number or degree of lift off events.

SUMMARY OF THE INVENTION

It is therefore an object of the present invention to provide a scanning technique for ultrasonic testing that addresses the loss of transducer contact with the test material.

It is a further object of the present invention to provide an adaptive scanning technique for ultrasonic testing that utilizes a realtime means for detecting the occurrence of lift off of the ultrasonic transducer.

It is a further object of the present invention to provide an adaptive scanning technique for ultrasonic testing that utilizes a realtime means of determining when lift off of the transducer has occurred and that takes steps to compensate for the effects of such transducer lift off on the reflected signal.

It is a further object of the present invention to provide an adaptive scanning technique for ultrasonic testing that utilizes a realtime means for determining when lift off of the transducer has occurred, and for relaying this information to a mechanical positioning system in a manner that regulates the transducer scanning parameters such as the scan speed and the mechanical compliance of the scanner with the test material.

It is a further object of the present invention to provide an adaptive scanning technique for ultrasonic testing that utilizes a realtime means for detecting the occurrence of lift off, and thereby prevents the misinterpretation of a reflected signal and/or prevents the loss of information, that would prompt the retesting of the material, and as a result, to significantly reduce the time required to scan the material.

The present invention achieves the above objects by providing an ultrasonic adaptive scanning technique and system that detects when transducer lift off occurs by identifying a lift off reflected signal, and analyzing this signal to determine a proper response either in the mechanical positioning system or in the speed with which the mechanical positioning system operates. When lift off occurs, the system is designed to adapt an otherwise automatic scanning sequence in a manner that compensates for the cause of the lift off of the transducer.

Other objects and characteristics of the present invention will become apparent in the disclosure contained below and the specifications and claims as hereinafter described.

BRIEF DESCRIPTION OF THE DRAWINGS

FIG. 4A is a detailed view of a typical ultrasonic transducer configuration in full mechanical contact with a test material.

FIG. 4B is a detailed view of a typical ultrasonic transducer configuration shown experiencing partial lift off.

FIG. 4C is a detailed view of a typical ultrasonic transducer configuration shown experiencing total lift off.

DESCRIPTION OF A PREFERRED EMBODIMENT

Figure 1:
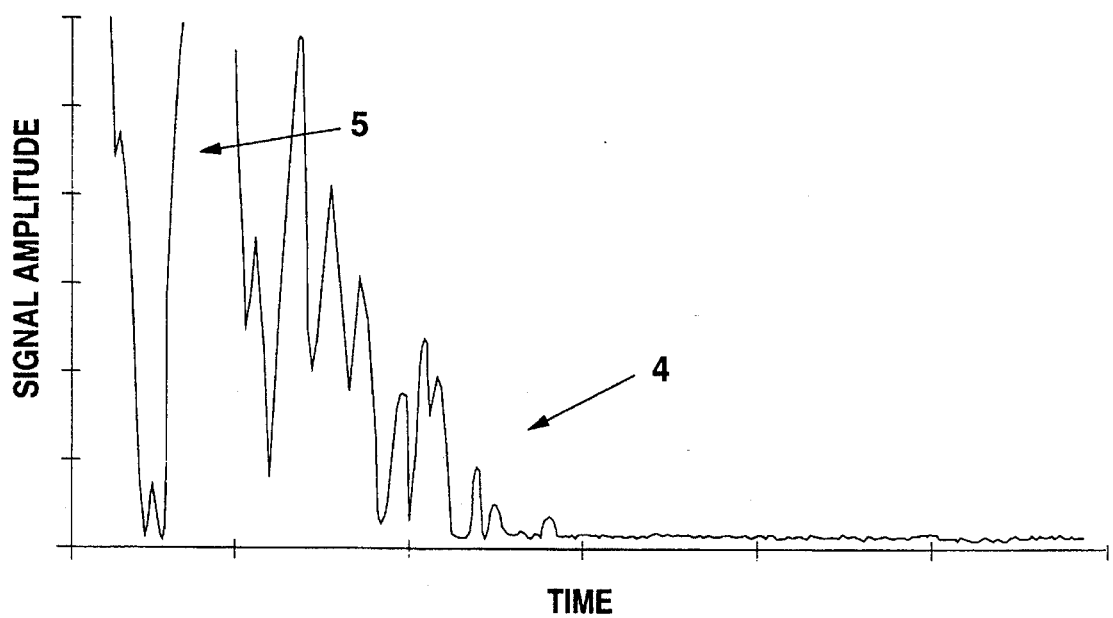
FIG. 1 is a graphic representation of a very high amplitude/early time ultrasonic signal return that is typical of a partial lift off of a transducer from the test material.

Reference is made first to FIG. 1 for a description of a graphic representation of the typical response of an ultrasonic transducer to partial lift off of the transducer from the material under test. The amplitude of return signal (4) is disposed on the vertical axis of FIG. 1, and the timing of return signal (4) is disposed on the horizontal axis. The time factor on the horizontal axis could be correlated to a position or distance variable depending upon the scanning technique and tracking system.

When an ultrasonic transducer encounters a partial lift off as a result of, for example, an irregularity in the surface of the material, a very high amplitude/early time signal (5) is experienced as shown in the first portion of the graph in FIG. 1. It is the identification of this high amplitude/early time signal (5) typical of partial lift off that is one object of the present invention. Once detected, this information is fed back to the controls of the mechanical positioning and contact force controlling means for scanning the transducer across the material. This information can also be used to control the speed with which the scan occurs. As soon as high amplitude/early time signal (5), such as that shown in FIG. 1, is detected the speed of the scan can be reduced until such high amplitude signal (5) has been diminished by appropriate adjustments to the mechanical positioning system.

Figure 2:
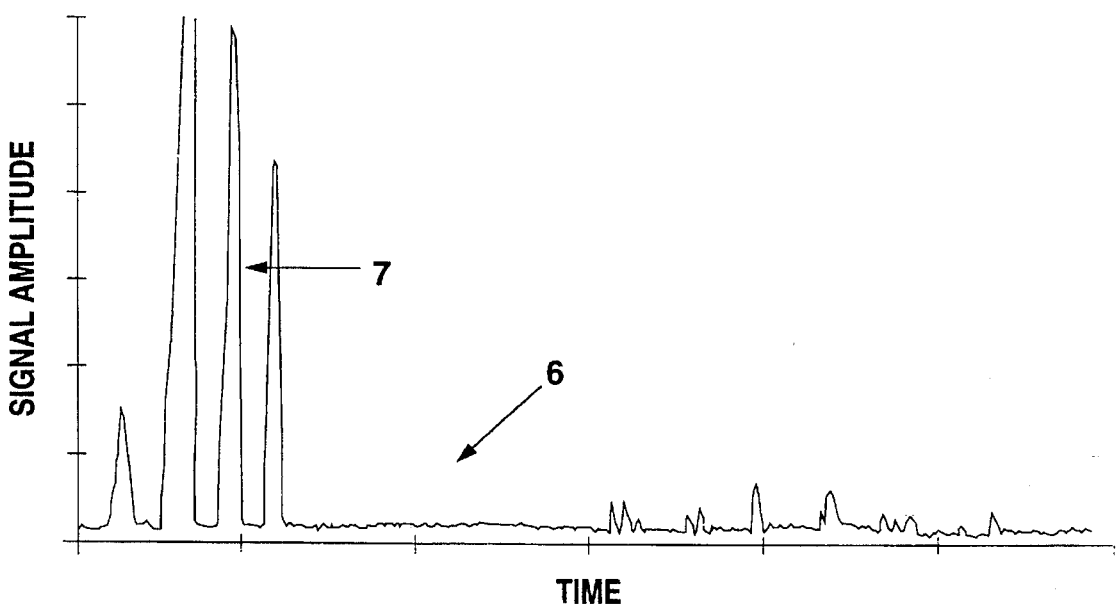
FIG. 2 is a graphic representation of the high amplitude/early time ultrasonic reverberation typical of a total lift off of a transducer from the test material.

Reference is now made to FIG. 2 for a description of a graphic representation of a similar lift off occurrence also the subject of this invention. FIG. 2, as with FIG. 1, discloses the amplitude of a reflected/generated return signal (6) on the vertical axis, and a time variable on the horizontal axis. FIG. 2 is a typical output for return signal (6) from an ultrasonic transducer scan that encountered a total lift off of the transducer. This signal (6) is typified by the reverberation of the return signal as seen by the periodic intervals of high amplitude (7) throughout the early part of the scan. As in FIG. 1, signal (6) here shows a high amplitude/early time return, but is distinguishable from the signal shown in FIG. 1 by its reverberation (7).

The information obtained by the standard ultrasonic receiving equipment is provided to the position tracking system and in conjunction with the specialized controller of the present invention, will appropriately direct the system to re-establish contact between the transducer and material being tested. As with the situation described in FIG. 1, the scanning speed can be reduced in order to establish contact and proceed with the rest of the scan and/or return to re-scan an area.

Figure 3:
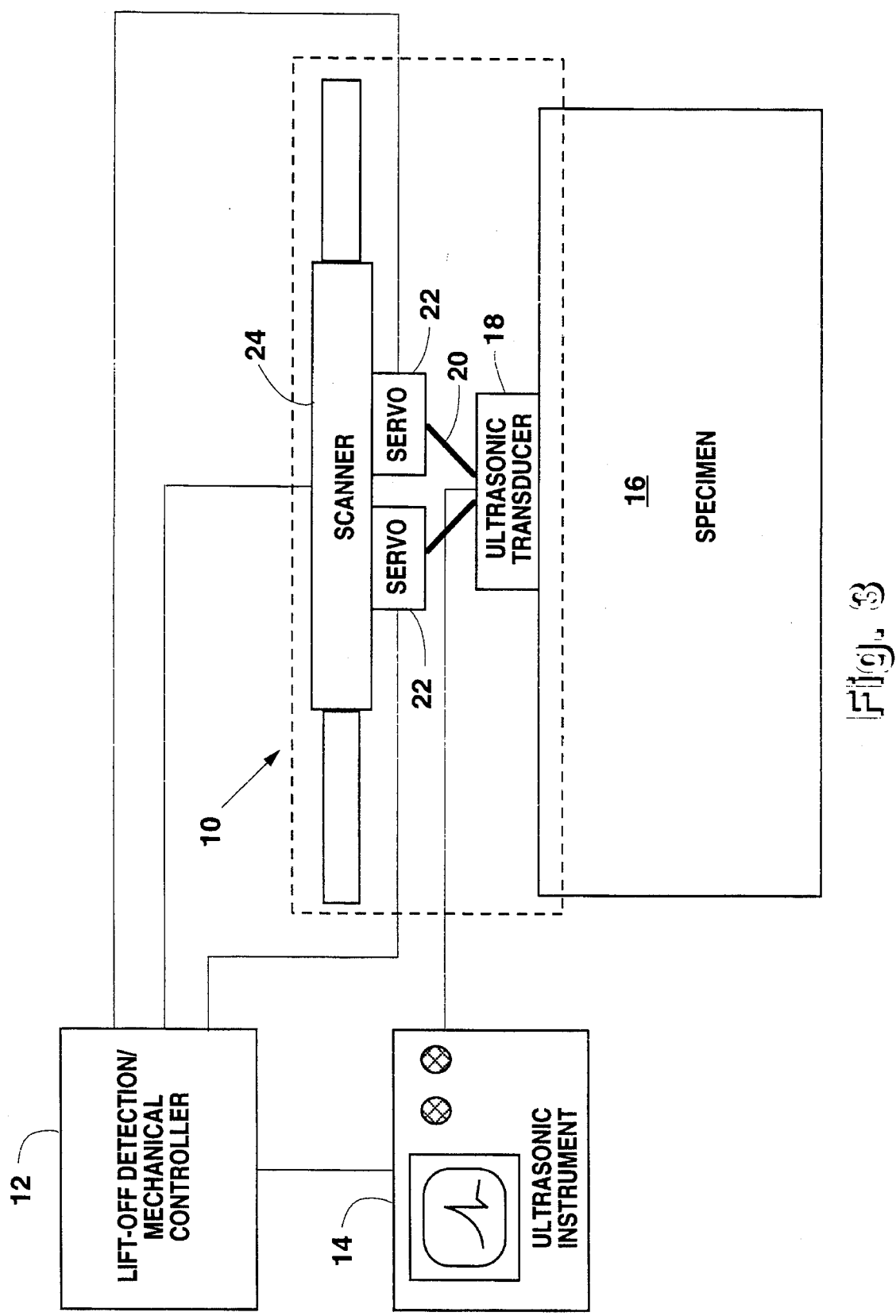
FIG. 3 is a schematic diagram showing the components of the system of the present invention.

Reference is now made to FIG. 3 for a detailed description of the assembly of an apparatus appropriate for the implementation of the method of the present invention. The system involves three primary component groups. First is ultrasonic scanning assembly (10), comprised of ultrasonic transducer (18) and mechanical positioning assembly (24). Controlling this scanning assembly (10) is the second primary component group, lift off detection/mechanical controller system (12) that receives the necessary information regarding lift off events and converts this information into appropriate changes in the mechanical compliance control of scanning assembly (10) by way of servos (22) attached through control arms (20) to ultrasonic transducer (18).

The third primary component group of the overall system is ultrasonic instrumentation (14) that collects not only the pertinent information on the specimen indicative of the expected anomalies and irregularities in the material, but also serves to collect the information that is interpreted as a partial or a total lift off of the transducer, and transfers this information to lift off detection/mechanical controller system (12).

Ultrasonic scanning assembly (10) is positioned proximate to specimen (16) being tested, and utilizes a typical ultrasonic transducer (18) that is appropriately mounted on movable scanning platform (24). Platform (24) allows transducer (18) to be systematically moved across and about the surface of specimen (16). There are any number of platforms (24) known in the art that are capable of achieving this systematic scan. The only requirements of such a platform (24) for the purposes of this invention are that it provide a two dimensional horizontal motion capability, as well as a variable vertical force capability that can change the contact force between transducer (18) and specimen (16). Both of these functions are typically achieved by means of servos (22) appropriately positioned to move transducer (18) about the surface of specimen (16). Platform (24) may be suspended above specimen (16) under test in a manner that allows either specimen (16) to move below platform (24) or platform (24) itself to traverse across the top of specimen (16). The only additional requirement on the structure of platform (24) is that each of these motions be speed controllable to a degree necessary to compensate for occurrences of lift off.

Ultrasonic instrumentation (14) is connected to ultrasonic transducer (18) by way of typical wiring for such systems. Instrumentation (14) is not unusual beyond its capacity to isolate reflected/generated signals that are typical of partial and total lift off situations. This is not so much a physical modification of standard instrumentation used to make such measurements, but an adaptation of the programming or the signal interpretation means incorporated in instrumentation (14) and the signal display. Ideally, ultrasonic instrumentation (14) would be programmed to recognize high amplitude/early time signal variations of both the type shown in FIG. 1 and the type shown in FIG. 2, and to correlate such patterns of reflected/generated signal with typical partial and total lift off occurrences. Given a sufficient data bank of correlated signals, ultrasonic instrumentation (14) can then transmit instructions to lift off detection/mechanical controller system (12) such that it can adapt or compensate scanning assembly (10) for these partial or total lift offs.

Standard ultrasonic instrumentation (14) is available that may be programmed to detect threshold signal amplitudes and to correlate certain amplitude signals with a time value. The present invention adds a sequence of program steps whereby a particular pattern of certain amplitude signals is recognized as a partial or total lift off event.

A typical ultrasonic transducer (18) transmits an ultrasonic pulse which starts the timing for the received signal. If the return signal amplitude exceeds a predetermined level within a certain time period from the start of the signal, a lift off event is recognized. The programming of instrumentation (14) in the present invention then detects subsequent signal amplitudes (again within a certain time period) and determines if any regularity (reverberation) exists. A comparison between the amplitude/time pattern of the received signal and a number of stored lift off signal patterns can be made to better characterize the degree of lift off. Instrumentation (14) then signals lift off detection/mechanical controller (12) that a lift off has occurred. This signal may include time values indicative of the start and duration of the lift off event, as well as indications of the degree of lift off (partial or total).

Lift off detection/mechanical controller (12) may be a typical controller device for ultrasonic scanning that has been adapted to receive the above described specific instructions derived by ultrasonic instrumentation (14). The three variables of horizontal positioning, vertical force, and speed, which are typically altered in a manual manipulation of ultrasonic transducer (18), can be automatically altered according to the instructions received from ultrasonic instrumentation (14).

Detection/controller (12) first uses the start time value from instrumentation (14) to identify the horizontal position of the lift off event (X and Y values for example). In the preferred embodiment, the detection of such lift off events is typically immediate enough to compensate without backtracking in the scan. For high speed scans, however, it may be necessary to return to a position where a lift off event was initiated.

In any case, detection/controller (12) then uses the duration time value and the indication of the degree of lift off to define vertical force and speed values appropriate to compensate. Here again, stored correlations between duration/degree and force/speed are referenced to select the most appropriate scan parameter changes. The present invention contemplates systems of varying degrees of refinement from a system that simply reduces transducer speed and increases contact force for any detected lift off event to a more refined system that compares detected event signals with stored signal patterns and selects optimum transducer speeds and contact forces for specific horizontal positions on specimen (16).

For example, if ultrasonic instrumentation (14) determines by analyzing a received signal that a partial lift off has occurred, the scanning speed can be reduced and the vertical pressure between ultrasonic transducer (18) and specimen (16) can be increased so as to return transducer (18) to mechanical compliance with specimen (16). In some situations, it may even be appropriate for the mechanical compliance controller (24) to return transducer (18) to a previous horizontal position on specimen (16) whose ultrasonic characteristics were overridden or missed by the occurrence of lift off. In other words, it might be appropriate for the system to start over from its initial point on specimen (16) if a lift off event blocked an accurate reading of the ultrasonic signal at that point.

Reference is now made to FIGS. 4A–4C for a detailed description of the type of event that initiates either a partial or a total lift off of the ultrasonic transducer from the material. Two factors, the condition of the test material surface and inaccuracies in the mechanical positioning system, generally contribute to lift off of ultrasonic transducers. Both of these factors, however, can be compensated for by the same alteration of the three positioning platform parameters described above.

The condition of the surface of the material itself and the nature of the transducer riding across the material will, to a great extent, effect partial and sometimes even total lift off of the transducer. If the transducer scanning speed is generally high over a relatively smooth surface, then even a small anomaly in the surface of the material can create a momentary lift off that at high speed could pass uncompensated. For example, on an otherwise planar surface, a raised portion of the material as small as a fraction of the width of the transducer face could create lift off of a gap sufficient to provide a signal similar to that shown in FIG. 1. While the surface anomaly may not be sufficient to initiate a total lift off of the transducer, it would be enough to prevent the collection of any relevant data from that particular point in the material. The reflected/generated signal at that point would essentially be the high amplitude signal as shown in FIG. 1.

Inaccuracies in the mechanical positioning system of the transducer can also be a source of partial or total lift off. The servo mechanisms, and vertical and horizontal force controlling mechanisms which typically move the ultrasonic transducer across the material, are themselves subject to nonlinear transitions that can result in abrupt and sometimes inappropriate movement of the transducer. While efforts can be made to reduce these non-linear transitions by the mechanical positioning system, there will always be some inaccuracies in the tracking of the transducer. This system makes it possible to identify when these inaccuracies result in a partial or total lift off requiring compensation. As with a lift off that occurs as a result of surface irregularities, this information can be fed directly into the mechanical positioning controller so that it may appropriately adapt the horizontal position of the transducer, the speed with which the transducer is being scanned, and the force with which the transducer is maintained in compliance with the material.

FIG. 4A shows the preferred scanning condition where transducer (18) is held in mechanical contact with specimen (16) by control arms (20). Full mechanical contact insures that transmitted signal (30) penetrates the surface of specimen (16) without any immediate reflection. Anomaly (28) then reflects (32) a portion of the ultrasonic signal, while a remaining portion (34) passes. An accurate scan of specimen (16) can thus be achieved.

FIG. 4B shows a partial lift off event, perhaps caused by a slight surface irregularity or an inaccurate servo motion. In any event, a lack of full mechanical compliance between transducer (18) and specimen (16) results in a high amplitude/early time reflected signal (32) from the surface of specimen (16). This is detected and compensated for as described above.

FIG. 4C shows a full lift off event, perhaps caused by a major surface anomaly or a loss of servo vertical pressure. Complete loss of mechanical compliance, as shown results in a reverberating high amplitude/early time reflected signal (32) from the surface of specimen (16). As with the partial lift off event shown in FIG. 4B, this full lift off is detected and compensated for as described above.

While the foregoing discussion of the present invention has described an apparatus and method in relation to certain preferred embodiments, and specific details have been disclosed for the purpose of illustration, it will be apparent to those skilled in the art that the invention is open to additional embodiments and that the details of the descriptions above could be altered considerably without departing from the basic principles of the invention.

I claim:

1. A method for automatically maintaining mechanical contact between an ultrasonic transducer and the surface of a material during ultrasonic non-destructive evaluation of said material, comprising the steps of:

positioning said ultrasonic transducer in mechanical contact with said surface;

systematically moving said ultrasonic transducer about said surface;

transmitting an ultrasonic signal into said material from said ultrasonic transducer;

receiving reflected ultrasonic signals from said material;

analyzing said reflected ultrasonic signals and identifying within said reflected ultrasonic signals, patterns of signal amplitude, frequency and timing predetermined to be characteristic of a partial or a total loss of mechanical contact between said transducer and said surface; and if said partial or total loss of mechanical contact between said transducer and said surface has occurred, additionally performing the steps of:

identifying a plurality of predetermined motion parameter changes for said ultrasonic transducer to compensate for said partial or total loss of mechanical contact between said transducer and said surface;

implementing said motion parameter changes so as to return said ultrasonic transducer into mechanical contact with said surface.

2. The method for maintaining mechanical contact described in claim 1 wherein said step of analyzing said reflected ultrasonic signals comprises:

measuring a plurality of time correlated signal amplitude and frequency values for such reflected ultrasonic signals;

comparing said plurality of time correlated signal amplitude and frequency values with predetermined patterns of signal amplitude and frequency values characteristic of said partial loss of mechanical contact;

determining whether said plurality of time correlated signal amplitude and frequency values are indicative of an occurrence of said partial loss of mechanical contact;

comparing said plurality of time correlated signal amplitude and frequency values with predetermined patterns of signal amplitude and frequency values characteristic of said total loss of mechanical contact;

determining whether said plurality of time correlated signal amplitude and frequency values are indicative of an occurrence of said total loss of mechanical contact;

determining a tracking distance and a separation distance over which said partial or total loss of mechanical contact occurred; and determining a time period over which said partial or total loss of mechanical contact occurred.

3. The method for automatically maintaining mechanical contact described in claim 1 wherein said step of identifying a plurality of predetermined motion parameter changes comprises:

identifying a location on said surface where said partial or total loss of mechanical contact occurred;

determining a direction of movement necessary to return said transducer to said location;

determining a scanning speed adjustment necessary to prevent a repeat of said partial or total loss of mechanical contact; and determining a vertical force adjustment on said transducer necessary to prevent a repeat of mechanical said partial or total loss of contact.

4. The method for automatically maintaining mechanical contact described in claim 1 wherein said step of implementing said motion parameter changes comprises:

moving said ultrasonic transducer about said surface to repeat said steps of transmitting an ultrasonic signal and receiving reflected ultrasonic signals for a portion of said surface where said partial or total loss of mechanical contact occurred;

maintaining a scanning speed necessary to prevent said partial or total loss of mechanical contact;

maintaining a vertical force on said transducer necessary to prevent said partial or total loss of mechanical contact; and recording occurrences of said partial or total loss of contact and said motion parameter changes implemented to compensate for said partial or total loss of mechanical contact.

5. A method for automatically maintaining mechanical contact between an ultrasonic transducer and the surface of a material during ultrasonic non-destructive evaluation of said material comprising the steps of:

positioning said ultrasonic transducer in mechanical contact with said surface;

systematically moving said ultrasonic transducer about said surface;

transmitting an ultrasonic signal into said material from said ultrasonic transducer;

receiving reflected ultrasonic signals from said material;

measuring a plurality of time correlated signal amplitude and frequency values for said reflected ultrasonic signals;

comparing said plurality of time correlated signal amplitude and frequency values with predetermined patterns of signal amplitude and frequency values characteristic of a partial loss of mechanical contact between said ultrasonic transducer and said surface;

determining whether said plurality of time correlated signal amplitude and frequency values are indicative of an occurrence of said partial loss of mechanical contact;

comparing said plurality of time correlated signal amplitude and frequency values with predetermined patterns of signal amplitude and frequency values characteristic of said total loss of mechanical contact between said ultrasonic transducer and said surface;

determining whether said plurality of time correlated signal amplitude and frequency values are indicative of an occurrence of said total loss of mechanical contact; and if said partial or total loss of mechanical contact between said transducer and said surface has occured, additionally performing the steps of:

determining a tracking distance and a separation distance over which said partial or total loss of mechanical contact occurred;

determining a time period over which said partial or total loss of mechanical contact occurred;

identifying a location on said surface where said partial or total loss of mechanical contact occurred;

determining a direction of movement necessary to return said transducer to said location;

determining a scanning speed adjustment necessary to prevent a repeat of said partial or total loss of mechanical contact;

determining a vertical force adjustment on said transducer necessary to prevent a repeat of said partial or total loss of mechanical contact;

moving said ultrasonic transducer about said surface to repeat said steps of transmitting and receiving ultrasonic signals for a portion of said surface where said partial or total loss of mechanical contact occurred;

maintaining a scanning speed necessary to prevent said partial or total loss of mechanical contact;

maintaining a vertical force on said transducer necessary to prevent said partial or total loss of mechanical contact; and recording occurrences of said partial or total loss of contact and motion parameter changes implemented to compensate for said partial or total loss of mechanical contact.

* * * * *